United States Patent
Timken et al.

(10) Patent No.: US 9,254,450 B2
(45) Date of Patent: *Feb. 9, 2016

(54) ALKYLATION PROCESS UNIT COMPRISING A FRACTIONATION UNIT FOR SEPARATING HYDROGEN GAS AND HYDROGEN CHLORIDE

(71) Applicants: Hye Kyung Cho Timken, Albany, CA (US); Robert Fletcher Cleverdon, Walnut Creek, CA (US); Bong-Ku Chang, Novato, CA (US); Donald Henry Mohr, Orinda, CA (US); Christine Marie Phillips, Pleasant Hill, CA (US)

(72) Inventors: Hye Kyung Cho Timken, Albany, CA (US); Robert Fletcher Cleverdon, Walnut Creek, CA (US); Bong-Ku Chang, Novato, CA (US); Donald Henry Mohr, Orinda, CA (US); Christine Marie Phillips, Pleasant Hill, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 76 days.

This patent is subject to a terminal disclaimer.

(21) Appl. No.: 14/157,968

(22) Filed: Jan. 17, 2014

(65) Prior Publication Data
US 2014/0134065 A1 May 15, 2014

Related U.S. Application Data

(60) Division of application No. 13/563,385, filed on Jul. 31, 2012, and a continuation of application No. 13/563,355, filed on Jul. 31, 2012, and a continuation of application No. 13/563,415, filed on Jul. 31, 2012, now Pat. No. 8,704,018, and a continuation of application No. 13/901,935, filed on May 24, 2013.

(51) Int. Cl.
| | |
|---|---|
| *B01J 19/00* | (2006.01) |
| *B01J 19/24* | (2006.01) |
| *B01D 3/00* | (2006.01) |
| *C07C 2/58* | (2006.01) |
| *C07C 5/02* | (2006.01) |
| *B01J 31/02* | (2006.01) |
| *C10G 29/20* | (2006.01) |
| *B01J 35/12* | (2006.01) |

(Continued)

(52) U.S. Cl.
CPC ............ *B01D 3/009* (2013.01); *B01J 31/0277* (2013.01); *C07C 2/58* (2013.01); *C07C 5/02* (2013.01); *C10G 29/205* (2013.01)

(58) Field of Classification Search
CPC ............ B01J 19/00; B01J 19/24; B01J 35/12; B01J 2219/00002; B01J 2219/00042; B01J 2219/00047; B01D 3/00; C10G 7/00; C10L 1/00; C10L 1/04
See application file for complete search history.

(56) References Cited

U.S. PATENT DOCUMENTS

| | | |
|---|---|---|
| 2,487,867 A | 11/1949 | Griffen, Jr |
| 5,421,167 A | 6/1995 | Verma |

(Continued)

OTHER PUBLICATIONS

Sinnott, R.K., Chemical Engineering Design, Coulson & Richardson's Chemical Engineering, vol. 6, Fourth Edition, pp. 5, (2005).

*Primary Examiner* — Natasha Young
(74) *Attorney, Agent, or Firm* — Susan M. Abernathy

(57) ABSTRACT

We provide an alkylation process, comprising: separating and recycling a hydrogen gas and a hydrogen chloride from an offgas of a hydrogenation reactor; wherein the hydrogen gas is recycled to the hydrogenation reactor; and wherein the hydrogen chloride is recycled to an alkylation reactor. We also provide an alkylation process unit for performing this process.

17 Claims, 6 Drawing Sheets

An Alkylation Unit with Catalyst Hydro-Regeneration, Hydrogen Recycle, and Hydrogen Chloride Recovery

(51) Int. Cl.
   *C10G 7/00*    (2006.01)
   *C10L 1/00*    (2006.01)
   *C10L 1/04*    (2006.01)

(56) References Cited

U.S. PATENT DOCUMENTS

| | | | |
|---|---|---|---|
| 5,637,207 A | 6/1997 | Hsing et al. | |
| 6,395,945 B1 | 5/2002 | Randolph | |
| 7,432,408 B2 | 10/2008 | Timken et al. | |
| 7,432,409 B2 | 10/2008 | Elomari et al. | |
| 7,553,999 B2 | 6/2009 | Elomari et al. | |
| 7,569,740 B2 | 8/2009 | Elomari et al. | |
| 7,576,252 B2 | 8/2009 | Elomari et al. | |
| 7,651,970 B2 | 1/2010 | Elomari et al. | |
| 7,678,727 B2 | 3/2010 | Harris et al. | |
| 7,691,771 B2 | 4/2010 | Harris et al. | |
| 7,727,925 B2 | 6/2010 | Elomari et al. | |
| 7,732,363 B2 | 6/2010 | Elomari et al. | |
| 7,732,651 B2 | 6/2010 | Driver et al. | |
| 7,825,055 B2 | 11/2010 | Elomari et al. | |
| 7,919,664 B2 | 4/2011 | Hommeltoft et al. | |
| 7,923,593 B2 | 4/2011 | Hommeltoft et al. | |
| 7,923,594 B2 | 4/2011 | Hommeltoft | |
| 7,955,495 B2 | 6/2011 | Hommeltoft et al. | |
| 8,101,809 B2 | 1/2012 | Elomari et al. | |
| 8,124,821 B2 | 2/2012 | Elomari et al. | |
| 2009/0020090 A1 | 1/2009 | Ryder et al. | |
| 2009/0071871 A1 | 3/2009 | Joensen et al. | |
| 2009/0242840 A1 | 10/2009 | Olschimke et al. | |
| 2010/0147740 A1 | 6/2010 | Elomari et al. | |
| 2010/0270205 A1 | 10/2010 | Lopez et al. | |
| 2011/0155632 A1 | 6/2011 | Timken et al. | |
| 2011/0155640 A1 | 6/2011 | Timken et al. | |
| 2011/0226669 A1 | 9/2011 | Timken et al. | |
| 2011/0319694 A1 | 12/2011 | Timken et al. | |
| 2012/0024750 A1 | 2/2012 | Zhan et al. | |
| 2012/0108862 A1 | 5/2012 | Elomari et al. | |
| 2013/0066130 A1 | 3/2013 | Luo et al. | |
| 2013/0066132 A1 | 3/2013 | Cleverdon et al. | |
| 2013/0066133 A1 | 3/2013 | Cleverdon et al. | |
| 2014/0037512 A1* | 2/2014 | Timken et al. | 422/187 |

* cited by examiner

An Alkylation Unit with Catalyst Hydro-Regeneration, Hydrogen Recycle, and Hydrogen Chloride Recovery H₂ Recycle and HCl Recovery from Ionic Liquid Catalyst Hydrogenation, Comparison Case H₂ Recycle and HCl Recovery from Ionic Liquid Catalyst Hydrogenation H₂ Recycle and HCl Recovery from Ionic Liquid Catalyst Hydrogenation $H_2$ Recycle and HCl Recovery from Ionic Liquid Catalyst Hydrogenation Hydro-regeneration Process Without Hydrocarbon Extraction Solvent

ALKYLATION PROCESS UNIT COMPRISING A FRACTIONATION UNIT FOR SEPARATING HYDROGEN GAS AND HYDROGEN CHLORIDE

This application is a divisional of U.S. application Ser. No. 13/563,385, titled "HYDROGEN RECYCLE AND HYDROGEN CHLORIDE RECOVERY IN AN ALKYLATION PROCESS", which was filed on Jul. 31, 2012, herein incorporated in its entirety.

This application is a continuation of U.S. application Ser. No. 13/563,355, titled "ALKYLATION PROCESS WITH RECYCLE OF HYDROGEN AND RECOVERY OF HYDROGEN CHLORIDE", which was filed on Jul. 31, 2012, herein incorporated in its entirety.

This application is a continuation of U.S. application Ser. No. 13/563,415, titled "EXTRACTED CONJUNCT POLYMER NAPHTHA", which was filed on Jul. 31, 2012, herein incorporated in its entirety.

This application is a continuation of U.S. application Ser. No. 13/901,935, titled "ALKYLATION PROCESS UNIT WITH RECYCLE OF HYDROGEN AND RECOVERY OF HYDROGEN CHLORIDE", which was filed on May 24, 2013, herein incorporated in its entirety.

TECHNICAL FIELD

This application is directed to a process and process unit for improved hydrogen chloride and hydrogen recycling in an alkylation process using hydrogenation.

BACKGROUND

Improved processes and process units for recycling hydrogen and hydrogen chloride are desired in alkylation processes using hydrogenation.

SUMMARY

This application provides an alkylation process, comprising: separating and recycling a hydrogen gas and a hydrogen chloride from an offgas of a hydrogenation reactor; wherein the hydrogen gas is recycled to the hydrogenation reactor; and wherein the hydrogen chloride is recycled to an alkylation reactor.

This application also provides an alkylation process unit, comprising:
 a. a fractionation unit for separating a hydrogen gas and a hydrogen chloride from an offgas of a hydrogenation reactor that regenerates a used ionic liquid catalyst; and
 b. a first connection between the fractionation unit and the hydrogenation reactor for transmitting at least a portion comprising the hydrogen gas to the hydrogenation reactor; and
 c. a second connection between the fractionation unit and an alkylation reactor to transmit at least a second portion comprising the hydrogen chloride to the alkylation reactor.

DETAILED DESCRIPTION

Alkylation processes and alkylation process units are used to make alkylate products, including alkylated aromatics and alkylated isoparaffins. The alkylate products can have a broad range of uses including, for example, gasoline blending components, middle distillates, base oils, and petrochemical components. The alkylation catalysts used in these processes for alkylation often contain a chloride. Examples of alkylation catalysts are alumina/silica aerogels with metal chloride (e.g., zinc chloride), and Friedel-Crafts alkylation catalysts. Friedel-Crafts alkylation involves the alkylation of an aromatic ring or isoparaffin with an alkyl halide or any carbocationic intermediate using a strong Lewis acid catalyst. Examples of carbocationic intermediates are those derived from alkenes and a protic acid, Lewis acid, enones, and epoxides. Some ionic liquid catalysts are Friedel-Crafts catalysts.

In an alkylation process employing either reactants or catalysts comprising a chloride, where a hydrogenation reactor provides an offgas to an alkylation reactor, it is often preferred to maintain a desired level of chloride in the process as well as to utilize hydrogen efficiently. 'Offgas' is defined herein as a gaseous effluent from the hydrogenation reactor. 'Recycling' is defined herein as returning material to a previous stage in a cyclic process. 'Recovering' is defined herein as retaining either in a substantial amount or in full, as opposed to disposing or removing. A substantial amount is at least 50 wt %.

In one embodiment, the alkylation reactor uses an alkylation catalyst comprising a chloride.

Figure 3:
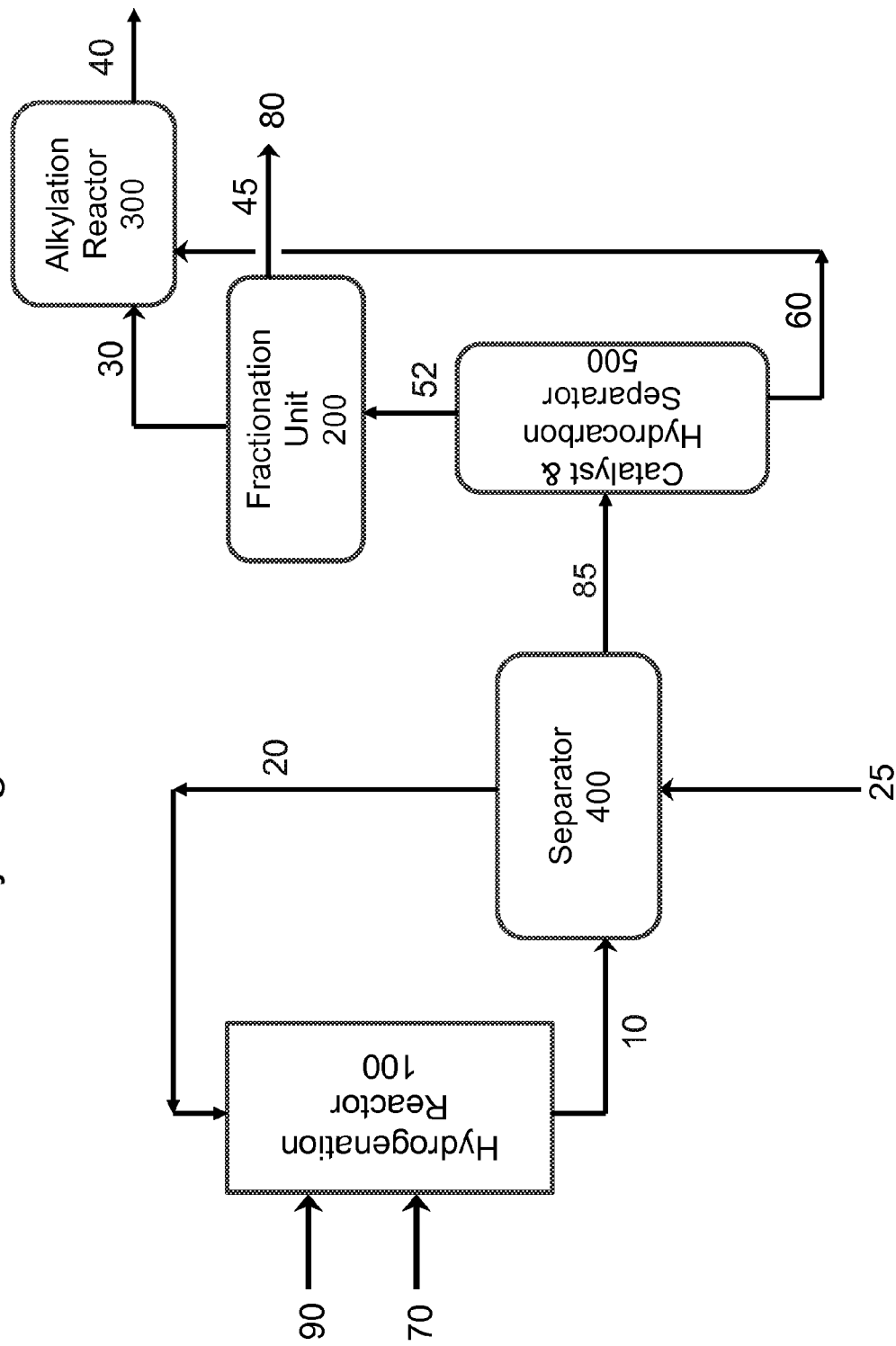
FIG. 3 is a diagram of an alternative alkylation process unit with catalyst hydro-regeneration, hydrogen recycle from a separator, and hydrogen chloride recovery.

Because the alkylation process includes a chloride, the hydrogenation unit liberates hydrogen chloride, which can build up to excessive levels and can suppress conversion in the hydrogenation reactor unless it is removed. Acid gas treating methods, for example, caustic aqueous scrubbing systems, can be used, but then the hydrogen chloride cannot be simply reused in the alkylation process. One example of how an acid gas treating method could be employed in an alkylation plant is shown in FIG. 3. If sodium hydroxide (NaOH) is used as the caustic reactant, for example, then the hydrogen chloride (HCl) is converted to sodium chloride (NaCl) and water, and it is not suitable for recycling into an ionic liquid alkylation process. The HCl destroyed in the HCl removal step can represent a significant operating cost when it must be compensated for by additional chloride injection into the alkylation process unit. It can also result in an aqueous waste stream that must be neutralized and disposed of in a water treatment system of the facility. Further, the recycle hydrogen must then be thoroughly dried before use in a hydrogenation reactor that uses or regenerates a water reactive catalyst.

Figure 1:
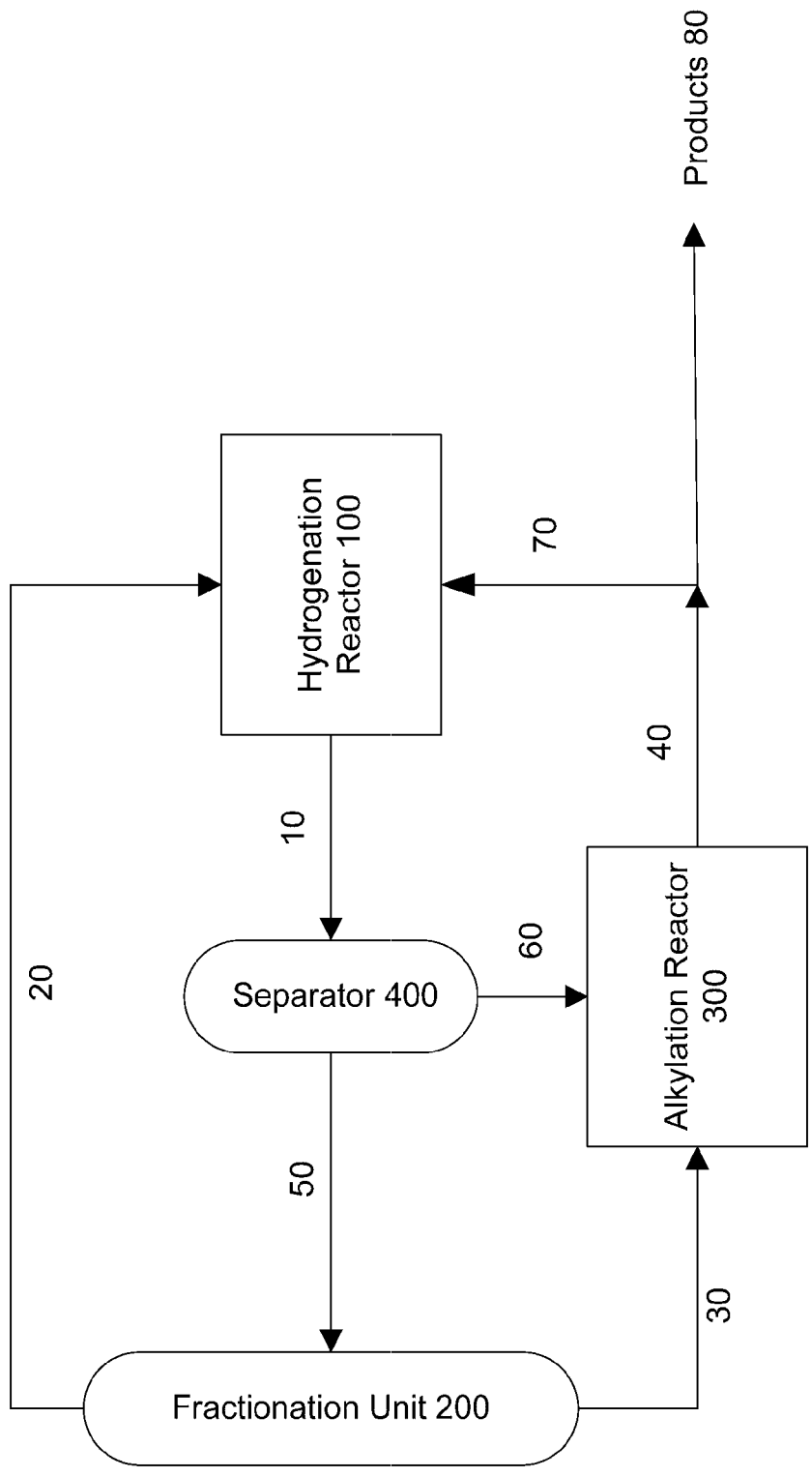
FIG. 1 is a diagram of an alkylation process unit with catalyst hydro-regeneration, hydrogen recycle and hydrogen chloride recovery; the comprehensive case.

Referring to FIG. 1, it is shown that a hydrogenation reactor (100) can be used continuously with little to no excessive hydrogen chloride build up, and with efficient hydrogen use, in an alkylation process using either reactants or catalysts with a chloride by the following process:

An effluent from an alkylation reactor (40) is separated into a portion of the effluent (70) and alkylate products (80). The portion of the effluent (70) is hydrogenated in a hydrogenation reactor (100). The hydrogenation reactor (100) produces a hydrogenated effluent (10) which is separated in a separator (400) into an offgas (50) and an ionic liquid catalyst stream (60). The offgas comprises hydrogen gas and hydrogen chloride. The ionic liquid catalyst stream (60) is optionally recycled to the alkylation reactor (300). The offgas (50) from the hydrogenation reactor (100), is separated in a fractionation unit (200) into a gas fraction comprising a hydrogen gas (20) and a light hydrocarbon fraction comprising a hydrogen chloride (30). At least a portion of the gas fraction comprising the hydrogen gas (20) is recycled to the hydrogenation reactor (100) and at least a portion of the light hydrocarbon fraction comprising hydrogen chloride (30) is recycled to the alkylation reactor (300).

Figure 2:
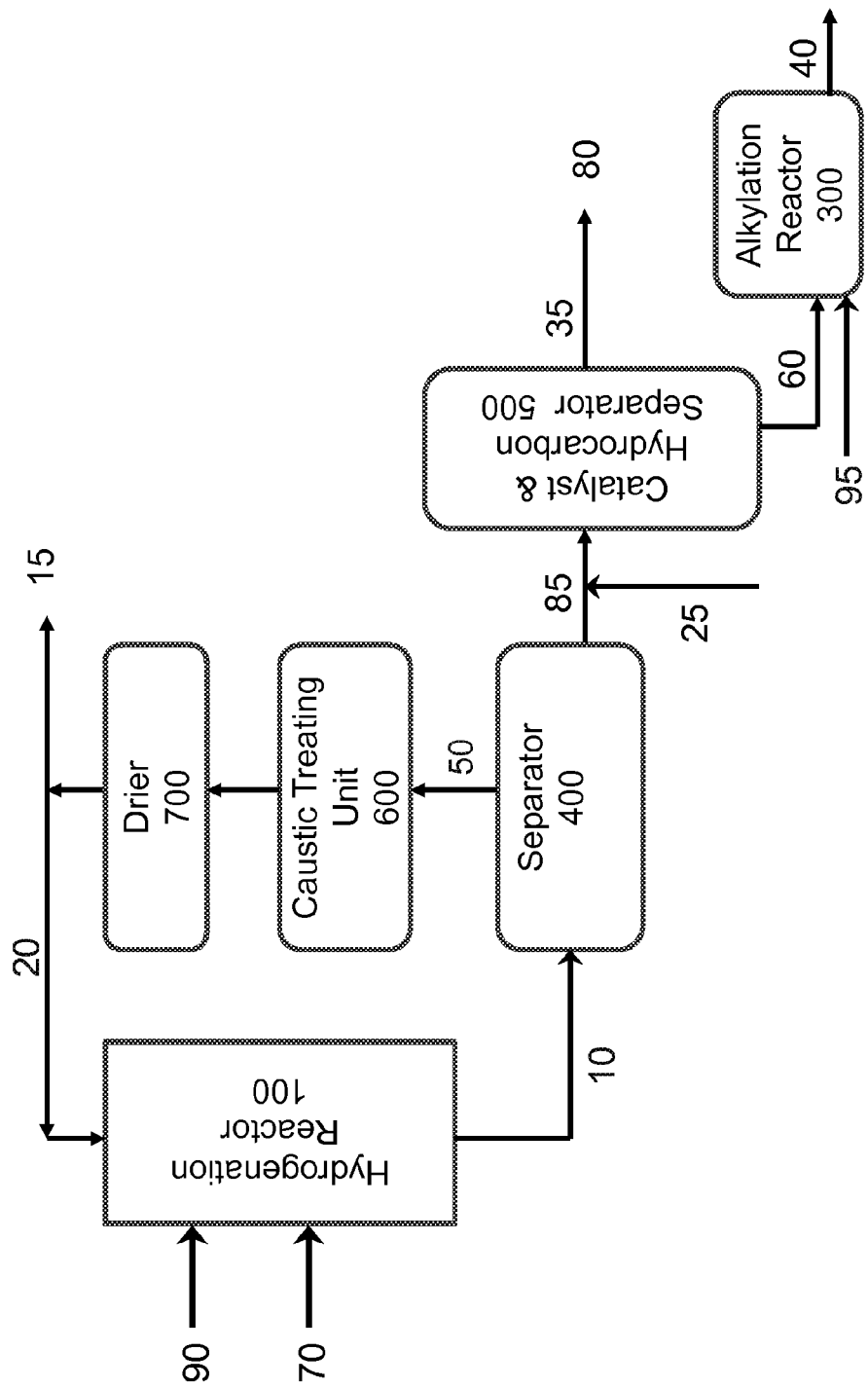
FIG. 2 is a diagram of an alkylation process unit with catalyst hydro-regeneration, hydrogen recycle, and hydrogen chloride removal by caustic scrubbing; the comparison case.

FIG. 2 shows a comparison process unit that does not recover a light fraction comprising a hydrogen chloride. In FIG. 2, hydrogen (90), and a portion of the effluent (70) comprising used catalyst from an alkylation reactor (300) is regenerated in a hydrogenation reactor. The hydrogenated effluent (10) is separated in a separator (400) that is a gas/liquid separation unit. The offgas (50) from the separator is subsequently treated in a caustic treating unit (600) and a drier (700), which remove the hydrogen chloride (as opposed to recovering) to produce a dry gas fraction comprising a hydrogen gas (20). The gas fraction comprising the hydrogen gas (20) is sent to the hydrogenation reactor. A recycle gas purge (15) stream removes excess hydrogen and light hydrocarbons from the process unit. The separated liquid (85) from the separator is mixed with a hydrocarbon extraction solvent (25) and the mixture is fed to an ionic liquid catalyst and hydrocarbon separator (500) which separates the mixture into a stream comprising both conjunct polymer and extraction solvent (35) and an ionic liquid catalyst stream (60). The stream comprising both conjunct polymer and extraction solvent (35) is sent to the refinery hydrocarbon pool of alkylate products (80). The ionic liquid catalyst stream (60) is recycled to the alkylation reactor (300). Chloride addition (95) is needed to replace the hydrogen chloride that is removed in the caustic treating unit (600).

FIG. 3 shows an improved process compared to FIG. 2, wherein hydrogen is recycled and hydrogen chloride is recovered and recycled efficiently. In FIG. 3, hydrogen (90), and a portion of the effluent (70), comprising used catalyst, from an alkylation reactor (300) are regenerated in a hydrogenation reactor. The hydrogenated effluent (10) is separated in a separator (400) that is a gas/liquid separation unit. A hydrocarbon extraction solvent (25) is fed to the separator (400) such that the separator (400) produces a separated liquid (85) and a gas fraction comprising a hydrogen gas (20). The gas fraction comprising the hydrogen gas (20) has a reduced amount of hydrogen chloride and the gas fraction comprising the hydrogen gas (20) is recycled to the hydrogenation reactor (100). The separated liquid (85) from the separator (400) comprises a hydrogen chloride. The separated liquid (85) is fed to an ionic liquid catalyst and hydrocarbon separator (500), which separates the separated liquid (85) into a hydrocarbon stream (52) and an ionic liquid catalyst stream (60). The hydrocarbon stream (52) is fed to a fractionation unit (200), where it is separated into two streams. One stream is a light hydrocarbon fraction comprising the hydrogen chloride (30). The second stream is extracted conjunct polymer naphtha (45). The light hydrocarbon fraction comprising the hydrogen chloride (30) is also recycled to the alkylation reactor (300). In this process the hydrogen chloride is recovered and recycled, rather than removed, as in FIG. 2. The extracted conjunct polymer naphtha (45) is sent to the refinery hydrocarbon pool of alkylate products (80).

Figure 4:
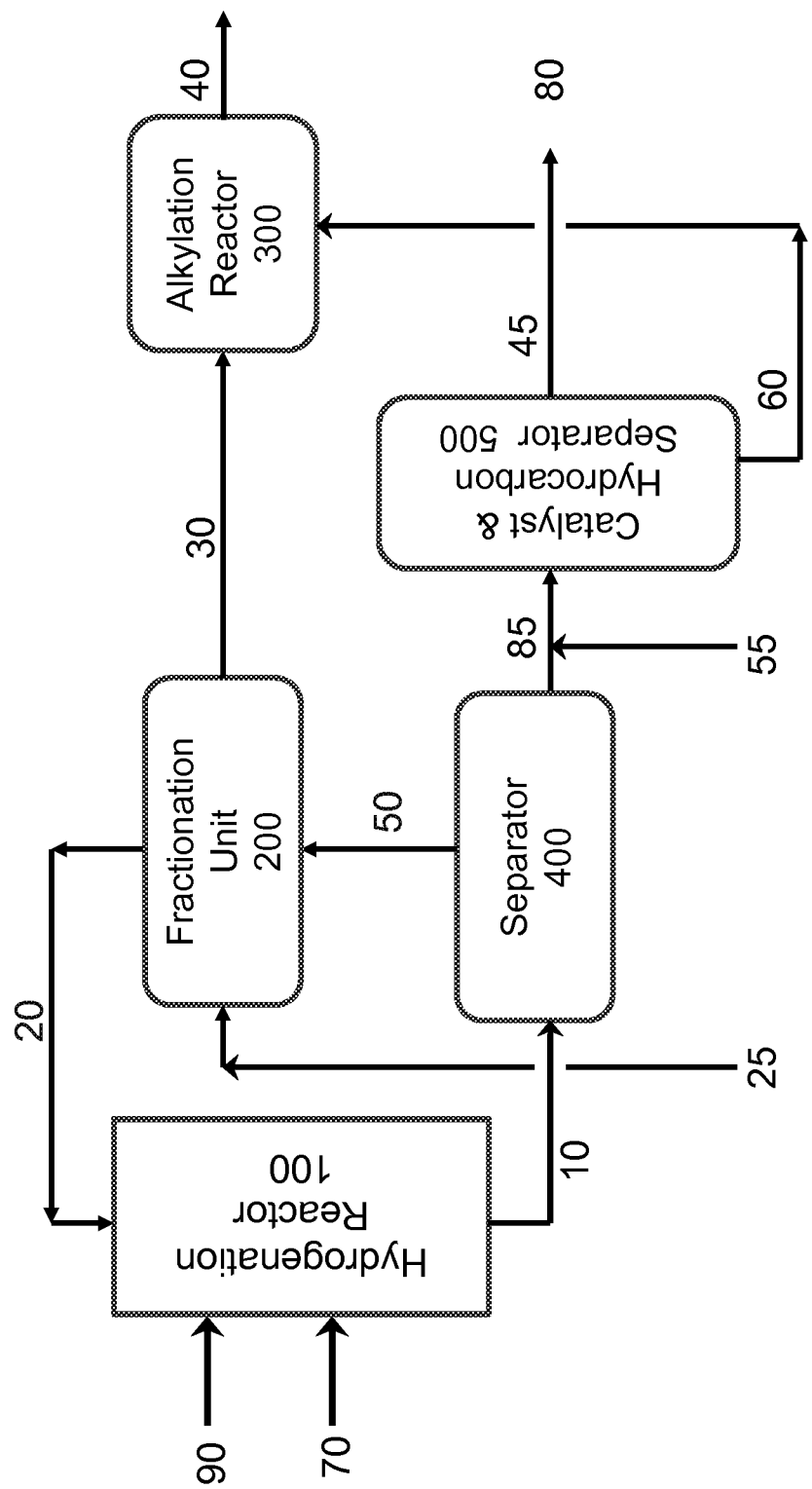
FIG. 4 is a diagram of a second alternative alkylation process unit with catalyst hydro-regeneration, hydrogen recycle and hydrogen chloride recovery.

FIG. 4 shows an alternative process wherein hydrogen is recycled and hydrogen chloride is recovered and recycled. In FIG. 4, hydrogen (90), and a portion of the effluent (70) comprising used catalyst from an alkylation reactor (300) are fed to a hydrogenation reactor (100). The hydrogenated effluent (10) from the hydrogenation reactor (100) is fed to a separator (400), which separates the hydrogenated effluent (10) into an offgas (50) and a separated liquid (85). The offgas (50) is fed to a fractionation unit (200). A hydrocarbon extraction solvent (e.g., an isoparaffin feed to the alkylation reactor) is also fed to the fractionation unit (200). The fractionation unit (200) fractionates the offgas (50) into a gas fraction comprising the hydrogen gas (20) and a light hydrocarbon fraction comprising a hydrogen chloride (30). The gas fraction comprising the hydrogen gas (20) is recycled to the hydrogenation reactor (100). The light hydrocarbon fraction comprising the hydrogen chloride (30) is recovered and recycled to the alkylation reactor. The separated liquid (85) from the separator (400) is mixed with a conjunct polymer extraction solvent (55) and the mixture is fed to an ionic liquid catalyst and hydrocarbon separator (500). The ionic liquid catalyst and hydrocarbon separator (500) separates the mixture of the separated liquid (85) and conjunct polymer extraction solvent (55) into extracted conjunct polymer naphtha (45) and an ionic liquid catalyst stream (60). The extracted conjunct polymer naphtha (45) is sent to the refinery hydrocarbon pool of alkylate products (80). The ionic liquid catalyst stream is recycled to the alkylation reactor (300).

Figure 5:
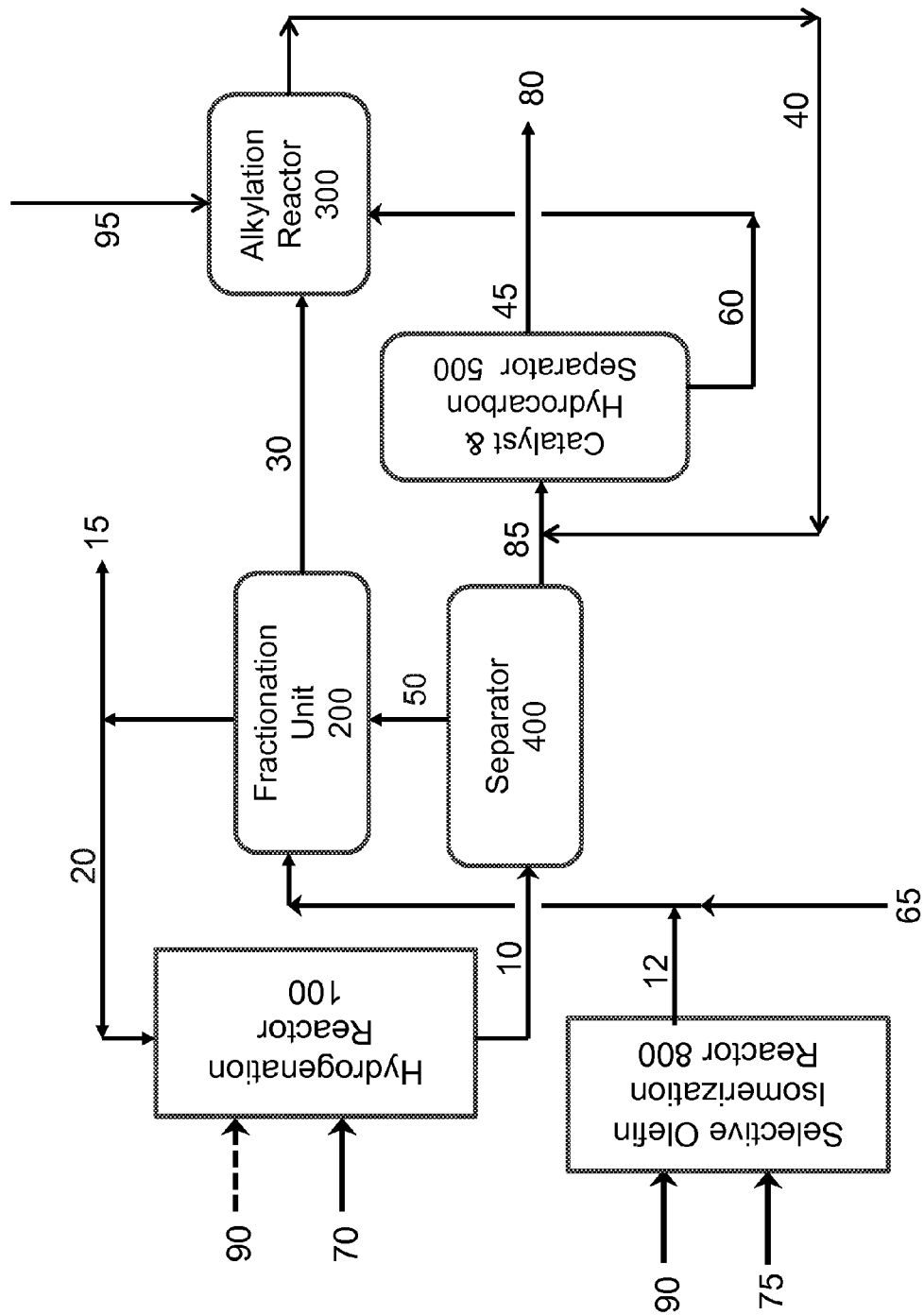
FIG. 5 is a diagram of a third alternative alkylation process unit with catalyst hydrogenation, hydrogen recycle and hydrogen chloride recovery. This diagram includes a selective olefin isomerization reactor.

FIG. 5 shows another alternative process wherein hydrogen is recycled and hydrogen chloride is recovered and recycled. In FIG. 5, a portion of the effluent (70) comprising used catalyst from an alkylation reactor (300) and optionally, hydrogen (90) are fed to a hydrogenation reactor (100). The hydrogenated effluent (10) from the hydrogenation reactor (100) is fed to a separator (400), which separates the hydrogenated effluent (10) into an offgas (50) and a separated liquid (85). In one embodiment, hydrogen (90) is not separately fed to the hydrogenation reactor (100), as all of the hydrogen needs for hydrogenation are supplied by a gas fraction comprising a hydrogen gas (20) from a fractionation unit (200). The offgas (50) is fed to the fractionation unit (200). Hydrogen (90) and an olefin feed (75) (e.g., 1-butene) are fed to a selective olefin isomerization reactor (800), wherein the olefin feed (75) is converted to isomerized olefins (12) (e.g., 2-butene). A hydrocarbon extraction solvent (25) (e.g., an isoparaffin feed (65) to be alkylated in the alkylation reactor) is mixed with the isomerized olefins (12) and the mixture is fed to the fractionation unit (200). The fractionation unit (200) fractionates the offgas (50) into a gas fraction comprising the hydrogen gas (20) and a light hydrocarbon fraction comprising a hydrogen chloride (30). The gas fraction comprising the hydrogen gas (20) is recycled to the hydrogenation reactor (100). Excess hydrogen and light hydrocarbons are removed in a recycle gas purge (15). The light hydrocarbon fraction comprising the hydrogen chloride (30) is recovered and recycled to the alkylation reactor. The separated liquid (85) from the separator (400) can be mixed with a conjunct polymer extraction solvent (55) or an effluent from an alkylation reactor (40), (as shown), and the mixture is fed to an ionic liquid catalyst and hydrocarbon separator (500). The ionic liquid catalyst and hydrocarbon separator (500) separates the mixture of the separated liquid (85) and one or more of conjunct polymer extraction solvent (55) and effluent from an alkylation reactor (40) into a stream comprised of extracted conjunct polymer naphtha (45) and an ionic liquid catalyst stream (60). The extracted conjunct polymer naphtha (45) is sent to the refinery hydrocarbon pool of alkylate products (80). The ionic liquid catalyst stream (60) is recycled to the alkylation reactor (300). As needed, chloride addition (95) can be made to the alkylation reactor (300).

Hydrogenation

Hydrogenation is a reduction reaction which results in an addition of hydrogen to a starting molecule. Hydrogenation changes the physical and chemical properties of the starting molecule. The addition of hydrogen can cleave the starting molecule, remove undesired impurities (e.g., sulfur, oxygen, nitrogen, conjunct polymer), or cause the starting molecule to undergo rearrangement (e.g., isomerization). Hydrogenation is often performed in the presence of a hydrogenation catalyst. One use of hydrogenation is to hydrogenate a used alkylation catalyst, such as a used acidic ionic liquid alkylation catalyst.

In one embodiment, an alkylation catalyst becomes deactivated during use and requires regeneration. The deactivation can be caused by, for example, the build-up of conjunct polymer in the alkylation catalyst. Regeneration can be achieved in a hydrogenation reactor (also referred to herein as a hydro-regeneration reactor). The hydrogenation removes the impurities, such as conjunct polymer, from the alkylation catalyst, thus increasing the acidity and ability of the catalyst to perform alkylations. In this embodiment, the hydrogenation reactor is used to regenerate the used alkylation catalyst.

In one embodiment, the catalyst used in the alkylation reactor is regenerated in the hydrogenation reactor. The hydrogenation reactor contacts the used catalyst with hydrogen and typically, a hydrogenation catalyst to regenerate the alkylation catalyst. In one embodiment, the hydrogenation catalyst is supported.

In one embodiment, the portion of the effluent comprises used catalyst which can be regenerated in the hydrogenation reactor. In one embodiment, the hydrogenation reactor contacts the used ionic liquid catalyst with hydrogen and a hydrogenation catalyst to regenerate the used ionic liquid catalyst. In one embodiment, zeolites or molecular sieves are added to the hydrogenation catalyst to improve the catalyst's performance. In one embodiment, the hydrogenation catalyst is supported. Typical support materials for the hydrogenation catalyst are kieselguhr, alumina, silica, and silica-alumina. Other support materials include alumina-boria, silica-alumina-magnesia, silica-alumina-titania and materials obtained by adding zeolites and other complex oxides thereto. When used, the support material has adequate mechanical strength and chemical stability at the hydrogenation reaction temperature.

In one embodiment, the hydrogenation is carried out in the presence of a catalyst which usually comprises a metal or non metal hydrogenation component on a porous support material, such as a natural clay or a synthetic oxide. Examples of metal hydrogenation components that can be used are Fe, Co, Ni, Ru, Rh, Pd, Pt, Ir, Os, Cr, Mn, Ti, V, Zr, Mo, W, and mixtures thereof. Examples of non metal hydrogenation components Te, As, and mixtures thereof. The hydrogenation components can be used singly or in combination.

The hydrogenation can be carried out over a broad range of hydrogen pressures, typically from about 50 to 5,000 psig. Hydrogenation conditions can include temperatures of −20° C. to 400° C., or 50° C. to 300° C.; and total pressures of atmospheric to 5,000 psig, or 50 to 2,500 psig. Hydrogenation contact times can be from 0.1 minute to 24 hours, such as 10 minutes to 12 hours. Feed to catalyst ratios during the hydrogenation can vary from 0.1 to 10 vol/vol/hour. A normal hydrocarbon can optionally be used as a solvent in the hydrogenation reactor.

Examples of hydrogenation of ionic liquid catalysts for regeneration, for example, are given in U.S. Pat. No. 7,691,771, U.S. Pat. No. 7,651,970, U.S. Pat. No. 7,678,727, and U.S. Pat. No. 7,825,055.

Separator for Hydrogenated Effluent

In one embodiment, the separator (400) separates the hydrogenated effluent, e.g., regenerated catalyst effluent streams, for efficient downstream processing. The separator can be configured in several different ways. For example, in FIG. 1, the separator separates the ionic liquid catalyst stream (60) from the regenerated catalyst effluent first. Then the offgas (50) stream containing hydrogen, hydrogen chloride, and hydrocarbon is sent to a fractionation unit (200) for further separation into a gas fraction comprising a hydrogen gas (20) and a light hydrocarbon fraction comprising a hydrogen chloride (30). In FIGS. 2, 4, and 5, the separator separates the regenerated catalyst effluent streams into an offgas (50) comprising hydrogen chloride gas and into a separated liquid (85). In FIG. 3, a hydrocarbon extraction solvent (25) was added to the separator to facilitate extraction of hydrogen chloride into a liquid stream. The separator (400) produces a gas fraction comprising a hydrogen gas (20), having a reduced level of hydrogen chloride, and a separated liquid (85). The separated liquid (85), comprising hydrogen chloride, hydrocarbon and ionic liquid catalyst, is sent to an ionic liquid catalyst and hydrocarbon separator (500). Examples of ionic liquid catalyst and hydrocarbon separators are centrifuges, liquid-liquid extractor, selective filters, settling tanks, and coalescers. Examples of suitable coalescers are described in U.S. Pat. No. 8,067,656.

Hydrocarbon Extraction Solvent

In one embodiment, the hydrogen chloride is extracted from the offgas of the hydrogenation reactor using a hydrocarbon extraction solvent. The hydrogen chloride can be extracted into the hydrocarbon extraction solvent, which is transmitted to the alkylation reactor. This embodiment is shown in FIGS. 3 through 5. The hydrocarbon extraction solvent can be any hydrocarbon that can serve as a solvent or reactant for the alkylation process. Examples of suitable extraction solvents for alkylation processes making alkylate gasoline are isobutane, alkylate gasoline, isomerized olefin, and mixtures thereof.

In one embodiment the hydrocarbon extraction solvent comprises an isomerized olefin. An example of an isomerized olefin is 2-butene. Processes for isomerizing olefins to make alkylate gasoline with improved RON are taught in U.S. Pat. No. 7,553,999.

In one embodiment, the hydrocarbon extraction solvent (25) is added to the hydrogenation reactor (100). In another embodiment, the hydrocarbon extraction solvent (25) is added to the hydrogenated effluent (10). In yet another embodiment, the hydrocarbon extraction solvent is added to either the separator (400) or the fractionation unit (200). In one embodiment, the hydrocarbon extraction solvent is fed into a stream selected from a hydrogenated effluent (10), an offgas (50) from a separator, or a combination thereof.

In FIG. 3, for example, the hydrocarbon extraction solvent is added to the hydrogenated effluent (10) either in the separator or prior to separating. In one embodiment, the effluent from the hydrogenation reactor can be separated by a series of a gas/liquid separator, a liquid/liquid separator, and a fractionation unit that is a distillation column. In one embodiment, the effluent from the hydrogenation reactor (100) is separated by the gas/liquid separator into: a) a gas fraction comprising a hydrogen gas (20) and b) separated liquid (85). The separated liquid comprises a light hydrocarbon fraction comprising a hydrogen chloride (30). In one embodiment, the liquid/liquid separator removes one liquid (regenerated alkylation catalyst), which is recycled back to an alkylation reactor, from a second liquid comprising the hydrocarbon extraction solvent and hydrogen chloride. The second liquid can be distilled in a fractionation unit into at least two streams, one being a portion of the light hydrocarbon fraction comprising the hydrogen chloride and the hydrocarbon extraction solvent, and the other being extracted conjunct polymer naphtha. In this example, the hydrocarbon extraction solvent can also be a reactant in the alkylation reactor. In this example, the hydrocarbon extraction solvent can be used to cool the effluent from the hydrogenation reactor.

The separating of the hydrogen gas and hydrogen chloride can be performed in a fractionation unit that is a distillation column. For example, in FIG. 5, the hydrocarbon extraction solvent comprises an isoparaffin (e.g., isobutane) and isomerized olefin. In this example, the hydrocarbon extraction solvent is mixed with the offgas from the hydrogenation reactor in the fractionation unit, e.g., a distillation column. In one embodiment, the isoparaffin and isomerized olefin are fed to the fractionation unit, used for the separating, at a location above where the offgas of the hydrogenation reactor is fed into the fractionation unit. In other words, the hydrocarbon extraction solvent is fed to the fractionation unit at a location above where the hydrogen gas and the hydrogen chloride are fed to the fractionation unit. In one embodiment, the hydrocarbon extraction solvent is fed to the fractionation unit in a counter current to the flow of offgas into the fractionation unit. In this example, and other embodiments, the hydrocarbon extraction solvent comprises an olefin and an isoparaffin. The olefin and the isoparaffin can be alkylated to make an alkylate gasoline blending component. In some embodiments, the alkylation catalyst is a chloroaluminate ionic liquid catalyst.

In one embodiment, the hydrocarbon extraction solvent comprising an olefin and an isoparaffin to be alkylated to make alkylate gasoline has an amount of isomerized olefin that is greater than 10 wt %, greater than 15 wt %, greater than 30 wt %, greater than 40 wt %, greater than 50 wt %, greater than 60 wt %, or greater than 70 wt % of the olefin in the hydrocarbon extraction solvent. For example, to make high RON alkylate gasoline blending component the olefin is greater than 40 wt %, greater than 50 wt %, and up to 100 wt % 2-butene, and the isoparaffin is isobutane.

In one embodiment, the hydrocarbon extraction solvent is fed at a vol/vol ratio of the hydrocarbon extraction solvent to the ionic liquid catalyst from 0.5 to 20.0, from 1.0 to 10.0, or from 1.5 to 5.0. The vol/vol ratio can be selected to provide the desired level of hydrogen chloride in the gas fraction comprising a hydrogen gas (20). The desired level of hydrogen chloride in the gas fraction comprising the hydrogen can be any level at least 25 wt % lower than a level of hydrogen chloride in the hydrogenated effluent, such as less than 1,000 wppm, less than 600 wppm, 500 wppm or less, less than 200 wppm, or less than 100 wppm. Alternatively, the vol/vol ratio can be selected to provide the desired wt % of the hydrogen chloride produced in the hydrogenation reactor that is recovered and recycled to the alkylation reactor. In some embodiments the desired level of hydrogen chloride in the gas fraction comprising the hydrogen is much reduced, such as at least 50 wt % up to 99% reduced.

Chloride Retention

In one embodiment, at least 80 wt % of the hydrogen chloride produced in the hydrogenation reactor is recovered and recycled to the alkylation reactor. For example, at least 85 wt %, at least 90 wt %, at least 94 wt %, up to 98 wt % of the hydrogen chloride can be recycled. In one embodiment, the chloride in the used catalyst is a hydrogen chloride co-catalyst.

By recycling the chloride, the amount of the chloride that needs to be added to the process is greatly reduced. Examples of chloride that may be added to the process to maintain the ionic liquid catalyst activity include hydrogen chloride, alkyl chloride, and metal chloride. In one example, the chloride added to the process is n-butyl chloride or t-butyl chloride. The chloride added to the process can be added at any point in the process, but is usually introduced into the alkylation reactor (300) as either a separate stream, or can be mixed with the ionic liquid catalyst stream (60) or the light hydrocarbon fraction comprising the hydrogen chloride (30).

Hydrogen Recycling

The hydrogen gas is separated and recycled to the hydrogenation reactor. Recycling the hydrogen can save significant cost associated with hydrogen supply. In one embodiment, the process additionally comprises removing a recycle gas purge (15) from the effluent from the fractionation unit (200). In one embodiment, the recycle gas purge (15) comprises an excess of the hydrogen gas from the offgas (50) of the hydrogenation reactor. This is demonstrated in FIG. 5. The excess hydrogen from the recycle gas purge (15) can then be utilized in other parts of an integrated refinery, stored, or used for other purposes. The removal of the excess hydrogen gas can eliminate concerns over excessive hydrogen in distillation column overhead systems.

In one embodiment, the process comprises compressing the recycled hydrogen gas in the gas fraction comprising the hydrogen gas (20) before recycling it to the hydrogenation reactor (100). The compression, when used, can use conventional compressor equipment and piping because the gas fraction comprising a hydrogen gas contains limited amounts of hydrogen chloride, and is thus not highly corrosive.

Separating

In one embodiment, the separating of the hydrogen gas and the hydrogen chloride from the offgas is done in a distillation column. In another embodiment, reactants to be alkylated in the alkylation reactor are also fed into the distillation column used to separate the hydrogen gas and the hydrogen chloride. This embodiment is shown in FIG. 4. The reactants can be fed either as a mixture or separately into the distillation column.

In one embodiment, wherein the separating is done in a distillation column into which is fed reactants to be alkylated, the reactants can be fed to the distillation column at a location above where the offgas from the hydrogenation reactor is fed to the distillation column. In one embodiment, the reactants to be alkylated, e.g., makeup isobutane and isomerized olefins are fed either separately or combined into the distillation column.

In one embodiment, shown in FIG. 5, the offgas from the hydrogenation reactor is first separated by a gas/liquid separator into a gas stream comprising hydrogen and hydrogen chloride and an ionic liquid catalyst stream comprising regenerated catalyst and extracted conjunct polymer naphtha. The offgas is mixed with isomerized olefins (e.g., 2-butene) and isobutane in a fractionation unit, where they are distilled into a gas fraction comprising the hydrogen gas, and a light hydrocarbon fraction comprising the hydrogen chloride. The light hydrocarbon fraction comprising the hydrogen chloride additionally comprises an isoparaffin (e.g., isobutane), isomerized olefins (e.g., 2-butene) and the hydrogen chloride, and the light hydrocarbon fraction is recycled to the alkylation reactor.

In one embodiment, the stream comprising the hydrogen chloride from the distillation column is mixed with a recycled stream comprising a mixture of a hydrogen chloride and a propane, from the alkylation reactor, before recycling the mixture back into the alkylation reactor.

In one embodiment, the light hydrocarbon fraction comprising the hydrogen chloride from the distillation column also comprises isobutane and olefins. This light hydrocarbon fraction can be mixed with a recycled stream from the ionic liquid reactor before recycling the mixture back into the alkylation reactor. The recycled stream from the ionic liquid reactor can, for example, comprise hydrogen chloride, propane, and isobutane.

Regenerated Alkylation Catalyst

In one embodiment, the hydrogenation reactor is used to regenerate a used alkylation catalyst. In one embodiment, the regenerated alkylation catalyst is recycled to the alkylation reactor. For example the regenerated alkylation catalyst can be a regenerated ionic liquid catalyst in the ionic liquid catalyst stream (60). This embodiment, where a regenerated alkylation catalyst that is an ionic liquid catalyst stream, is recycled to the alkylation reactor is shown in FIGS. 3, 4, and 5.

In one embodiment, an effluent from the hydrogenation reactor is separated in a first separator to produce a gas fraction comprising the hydrogen gas and a light hydrocarbon fraction comprising the hydrogen chloride. The gas fraction comprising the hydrogen gas is recycled to the hydrogenation reactor. The light hydrocarbon fraction is separated in a second separator to produce a stream comprising a regenerated alkylation catalyst (an ionic liquid catalyst, for example) and a lighter stream comprising one or more reactants, extracted conjunct polymer naphtha, and hydrogen chloride. The lighter stream is further separated in a distillation column to produce a top cut comprising hydrocarbon reactants and hydrogen chloride and a bottom cut comprising extracted conjunct polymer naphtha. The top cut is recycled to the alkylation reactor and the bottom cut is mixed with the alkylation products.

Ionic Liquid Catalyst

In one embodiment, the alkylation reactor uses an alkylation catalyst that is an ionic liquid catalyst. The ionic liquid catalyst is any ionic liquid which works effectively to perform an alkylation reaction with a chloride as a co-catalyst. The ionic liquid catalyst is an organic salt or mixture of salts. The ionic liquid catalyst can be characterized by the general formula Q+A−, wherein Q+ is an ammonium, phosphonium, boronium, iodonium, or sulfonium cation and A− is a negatively charged ion such as Cl−, Br−, ClO$_4^-$, NO$_3^-$, BF$_4^-$, BCl$_4^-$, PF$_6^-$, SbF$_6^-$, AlCl$_4^-$, TaF$_6^-$, CuCl$_2^-$, FeCl$_3^-$, HSO$_3^-$, RSO$_3^-$, SO$_3$CF$_3^-$, alkyl-aryl sulfonate, and benzene sulfonate (e.g., 3-sulfurtrioxyphenyl). In one embodiment the ionic liquid catalyst is selected from those having quaternary ammonium halides containing one or more alkyl moieties having from about 1 to about 12 carbon atoms, such as, for example, trimethylamine hydrochloride, methyltributylammonium halide, or substituted heterocyclic ammonium halide compounds, such as hydrocarbyl-substituted-pyridinium halide compounds for example 1-butylpyridinium halide, benzylpyridinium halide, or hydrocarbyl-substituted-imidazolium halides, such as for example, 1-ethyl-3-methyl-imidazolium chloride.

In one embodiment, the ionic liquid catalyst is an organic salt that is hygroscopic in nature and has a tendency to attract and hold water molecules from the surrounding environment. With these ionic liquid catalysts, in order to maintain the integrity of the ionic liquid catalyst and its catalytic performance, the organic salts from which the ionic liquid catalyst is synthesized, are thoroughly dried before the catalyst synthesis, and moisture-free conditions are maintained during the alkylation reaction.

In one embodiment the ionic liquid catalyst is selected from the group consisting of hydrocarbyl-substituted-pyridinium chloroaluminate, hydrocarbyl-substituted-imidazolium chloroaluminate, quaternary amine chloroaluminate, trialkyl amine hydrogen chloride chloroaluminate, alkyl pyridine hydrogen chloride chloroaluminate, and mixtures thereof. For example, the used ionic liquid catalyst can be an acidic haloaluminate ionic liquid, such as an alkyl substituted pyridinium chloroaluminate or an alkyl substituted imidazolium chloroaluminate of the general formulas A and B, respectively.

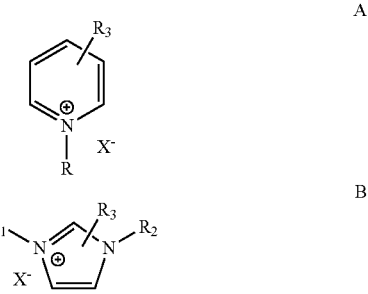

In the formulas A and B; R, R$_1$, R$_2$, and R$_3$ are H, methyl, ethyl, propyl, butyl, pentyl or hexyl group, X is a chloroaluminate. In another embodiment, R, R$_1$, R$_2$, and R$_3$ are methyl, ethyl, propyl, butyl, pentyl or hexyl group, and X is a chloroaluminate. In one embodiment the X is AlCl$_4^-$, Al$_2$Cl$_7^-$, or Al$_3$Cl$_{10}^-$. In the formulas A and B, R, R$_1$, R$_2$, and R$_3$ may or may not be the same. In one embodiment the ionic liquid catalyst is N-butylpyridinium heptachlorodialuminate [Al$_2$Cl$_7^-$]. In one embodiment the ionic liquid catalyst is 1-Ethyl-3-methylimidazolium tetrachloroaluminate [emim$^+$][AlCl$_4^-$].

Products

Alkylate products that can be produced by this process include alkylated aromatics and alkylated isoparaffins. The alkylate products can have a broad range of uses including, for example, as gasoline blending components, middle distillates, base oils, and petrochemical components. The gasoline blending components can have excellent properties, including high RONs and low RVP. The base oils can have excellent properties, including low pour points, low cloud points, and varied viscosity indexes and kinematic viscosities. The middle distillates can have unique branching properties, making some of them even suitable as jet fuel. Processes for making high quality alkylate gasoline blending components are described, for example, in earlier patent publications, including U.S. Pat. No. 7,432,408, U.S. Pat. No. 7,432,409, U.S. Pat. No. 7,553,999, U.S. Pat. No. 7,732,363, and US20110230692. Processes for making base oils are described, for example, in U.S. Pat. No. 7,569,740, U.S. Pat. No. 7,576,252, U.S. Pat. No. 8,124,821, U.S. Pat. No. 8,101,809, and patent application Ser. No. 12/966,638 (filed Dec. 13, 2010) and Ser. No. 12/966,738 (filed Dec. 13, 2010). Processes for making middle distillates are described, for example, in U.S. Pat. No. 7,923,593, U.S. Pat. No. 7,919,664, U.S. Pat. No. 7,955,495, and U.S. Pat. No. 7,923,594. Alkylated aromatic products and processes are described in U.S. Pat. No. 7,732,651.

In one embodiment, the effluent from an alkylation reactor (40) comprises alkylate products (80). In one embodiment, a propane product, an n-butane product, and an alkylate gasoline blending component product are separated from an effluent from the alkylation reactor (40).

Extracted Conjunct Polymer Naphtha

In one embodiment, the process additionally comprises separating an extracted conjunct polymer naphtha (45) from an effluent from the hydrogenation reactor and blending the extracted conjunct polymer naphtha into an alkylate gasoline. The extraction of the extracted conjunct polymer naphtha (45) can be performed in a catalyst & hydrocarbon separator (500) or in a fractionation unit (200). The hydrogenation of the conjunct polymer can improve the properties of the conjunct polymer made during the alkylation reaction such that it has a suitable boiling range and purity to be blended into high quality alkylate gasoline. Blending the extracted conjunct polymer naphtha (45) in this way can greatly reduce waste disposal and equipment costs. For example, incineration, neutralization, and storage equipment can be eliminated from the alkylation process unit.

The extracted conjunct polymer naphtha (45) from the offgas of the hydrogenation reactor can have a final boiling point less than 246° C. (475° F.), such as having a boiling range distribution from 90° F. to 474° F. (32° C. to 246° C.), from 95° F. to 460° F. (35° C. to 238° C.), from 100° F. to 450° F. (38 C to 232° C.), from 105° F. to 445° F. (41° C. to 229° C.), or from 110° F. to 440° F. (43° C. to 227° C.). The test method used for determining the boiling range distribution is ASTM D86-11b. In addition, the extracted conjunct polymer naphtha can have a low sulfur content (e.g., from 0.05 wt % to 0.5 wt %) a low bromine number (e.g., from <1 to 5), and a low chloride content (e.g., from 5 ppm to 500 ppm), even without additional treatment.

In one embodiment, the process produces unique alkylate gasoline products that comprise the extracted conjunct polymer naphtha (45) that has been hydrogenated and extracted from the hydrogenated effluent (10). In one embodiment, the alkylate gasoline comprises the extracted conjunct polymer naphtha (45) having a boiling point less than 246° C. (475° F.), and as further described above, extracted from the portion of the effluent (70).

The extracted conjunct polymer naphtha (45) from the offgas of the hydrogenation reactor can have a final boiling point less than 246° C. (475° F.), such as having a boiling range distribution from 100° F. to 474° F. (38° C. to 246° C.), from 120° F. to 460° F. (49° C. to 238° C.), from 130° F. to 450° F. (54° C. to 232° C.), or from 140° F. to 440° F. (60° C. to 227° C.). The test method used for determining the boiling range distribution is ASTM D2887-08. In addition, the extracted conjunct polymer naphtha can have a low sulfur content (e.g., from 0.05 wt % to 0.5 wt %) a low bromine number (e.g., from <1 to 5), and a low chloride content (e.g., from 5 ppm to 500 ppm), even without additional treatment.

In one embodiment, the process produces unique alkylate gasoline products that comprise the extracted conjunct polymer naphtha that has been hydrogenated and extracted from the hydrogenated effluent (10). In one embodiment, the alkylate gasoline comprises the extracted conjunct polymer naphtha having a boiling point less than 246° C. (475° F.), and as further described above, extracted from the used alkylation catalyst.

Alkylation Process Unit

The alkylation process unit is one designed to conduct the processes described herein. Process units performing these processes are shown in FIGS. 1, 3, 4, and 5. These process units all comprise a hydrogenation reactor and a fractionation unit fluidly connected to the hydrogenation reactor, a first connection between the fractionation unit and the hydrogenation reactor for transmitting at least a portion of the hydrogen gas to the hydrogenation reactor, and a second connection between the fractionation unit and the alkylation reactor to transmit at least a portion of the hydrogen chloride to the alkylation reactor. By "fluidly connected" it is meant that the connection provides a conduit wherein the contents move freely past one another and have the tendency to assume the shape of their container; a liquid or gas.

In one embodiment, the fractionation unit comprises a gas/liquid separator. In another embodiment, the fractionation unit comprises a distillation column. In yet another embodiment the fractionation unit comprises a gas/liquid separator and an ionic liquid catalyst and hydrocarbon separator. The ionic liquid catalyst and hydrocarbon separator can comprise a gravity separator, a coalescer, a liquid-liquid extractor, a distillation column, or combinations thereof.

In one embodiment, the alkylation process unit additionally comprises a compressor between the fractionation unit and the hydrogenation reactor. A compressor is a mechanical device that increases the pressure of a gas by reducing its volume. Examples of types of compressors are hermetically sealed, open, or semi-hermetic, centrifugal, diagonal, mixed-flow, axial-flow, reciprocating, rotary screw, rotary vane, scroll, diaphragm, and air bubble.

In one embodiment, the alkylation process unit additionally comprises a third connection between a product treatment unit and the second connection, wherein the stream comprising the hydrogen chloride, separated from the offgas of the hydrogenation reactor, is mixed with a recycled stream, from the product treatment unit, comprising a mixture of a gaseous hydrogen chloride and a propane. The product treatment unit is used to separate and refine the products produced by the process and may include further hydrotreatment and separation steps.

In one embodiment, the alkylation process unit additionally comprises an inlet wherein a hydrocarbon extraction solvent is fed to the fractionation unit or to a separator that is located between the hydrogenation reactor and the fractionation unit.

EXAMPLES

Example 1

Ionic Liquid Catalyst Comprising Anhydrous Metal Halide

Various ionic liquid catalysts made of metal halides such as $AlCl_3$, $AlBr_3$, $GaCl_3$, $GaBr_3$, $InCl_3$, and $InBr_3$ could be used for the catalytic processes. N-butylpyridinium chloroaluminate ($C_5H_5NC_4H_9Al_2Cl_7$) ionic liquid catalyst is an example used in our process. The catalyst has the following composition:

| | |
|---|---|
| Wt % Al | 12.4 |
| Wt % Cl | 56.5 |
| Wt % C | 24.6 |
| Wt % H | 3.2 |
| Wt % N | 3.3 |

Example 2

Alkylation of $C_4$ Olefin and Isobutane to Make Alkylate Gasoline with and without HCl Recycle Evaluation of $C_4$ olefins alkylation with isobutane was performed in a continuously stirred tank reactor using typical refinery mixed $C_4$ olefin feed and isobutane. An 8:1 molar mixture of isobutane and olefin was fed to the reactor while vigorously stirring. An ionic liquid catalyst was fed to the reactor via a second inlet port targeting to occupy 6 vol % in the reactor. A small amount of n-butyl chloride was added to produce anhydrous HCl gas. The average residence time (combined volume of feeds and catalyst) was about 4 minutes. The outlet pressure was maintained at 200 psig and the reactor temperature was maintained at 95° F. (35° C.) using external cooling.

The reactor effluent was separated with a gravity separator into a hydrocarbon phase and an ionic liquid catalyst phase. The hydrocarbon stream was further separated into multiple streams: a $C_3$ stream containing HCl, an $nC_4$ stream, an $iC_4$ stream and an alkylate gasoline stream. The alkylate product had 94 Research Octane Number and 410° F. (210° C.) end point. When the $C_3$ stream containing HCl was recycled to the alkylation reactor, we were able to lower the n-butyl chloride usage by 10% without affecting alkylate gasoline properties. This confirmed that recovering HCl with light hydrocarbon is an effective way to capture HCl and reuse.

Example 3

Isomerization of Olefin Feed, Alkylation, Regeneration of Ionic Liquid Catalyst by Hydrogenation and a Composition of Hydrogenation Reactor Offgas A refinery $C_3$ and $C_4$ olefin stream from a Fluid Catalytic Cracking Unit (FCC unit) was isomerized with a $Pd/Al_2O_3$ catalyst at 66° C. (150° F.) and 250 psig in the presence of hydrogen to produce isomerized $C_3$ and $C_4$ olefin feed with the composition shown in Table 1.

TABLE 1

| Composition of Olefin Feed | |
|---|---|
| Composition | Mol % |
| Propane, C3 | 13.3 |
| Propylene, C3= | 25.4 |
| 1-Butene, 1-C4= | 2.3 |
| 2-Butene, 2-C4= | 16.2 |
| Isobutylene, i-C4= | 6.7 |
| n-Butane, nC4 | 12.4 |
| Isobutane, iC4 | 22.2 |
| C5+ | 1.6 |
| Sum | 100.0 |

The isomerized olefin was alkylated with isobutane in a continuously stirred tank reactor. An 8:1 molar mixture of isobutane and olefin was fed to the reactor while vigorously stirring. An ionic liquid catalyst was fed to the reactor via a second inlet port targeting to occupy 6 vol % in the reactor. A small amount of n-butyl chloride was added to produce anhydrous HCl gas. The average residence time (combined volume of feeds and catalyst) was about 4 minutes. The outlet pressure was maintained at 200 psig and the reactor temperature was maintained at 95° F. (35° C.) using external cooling.

The alkylation reactor effluent was separated to a hydrocarbon stream and an ionic liquid catalyst stream. The ionic liquid catalyst was recycled back to the alkylation reactor and the conjunct polymer level of the ionic liquid catalyst was gradually increased.

Figure 6:
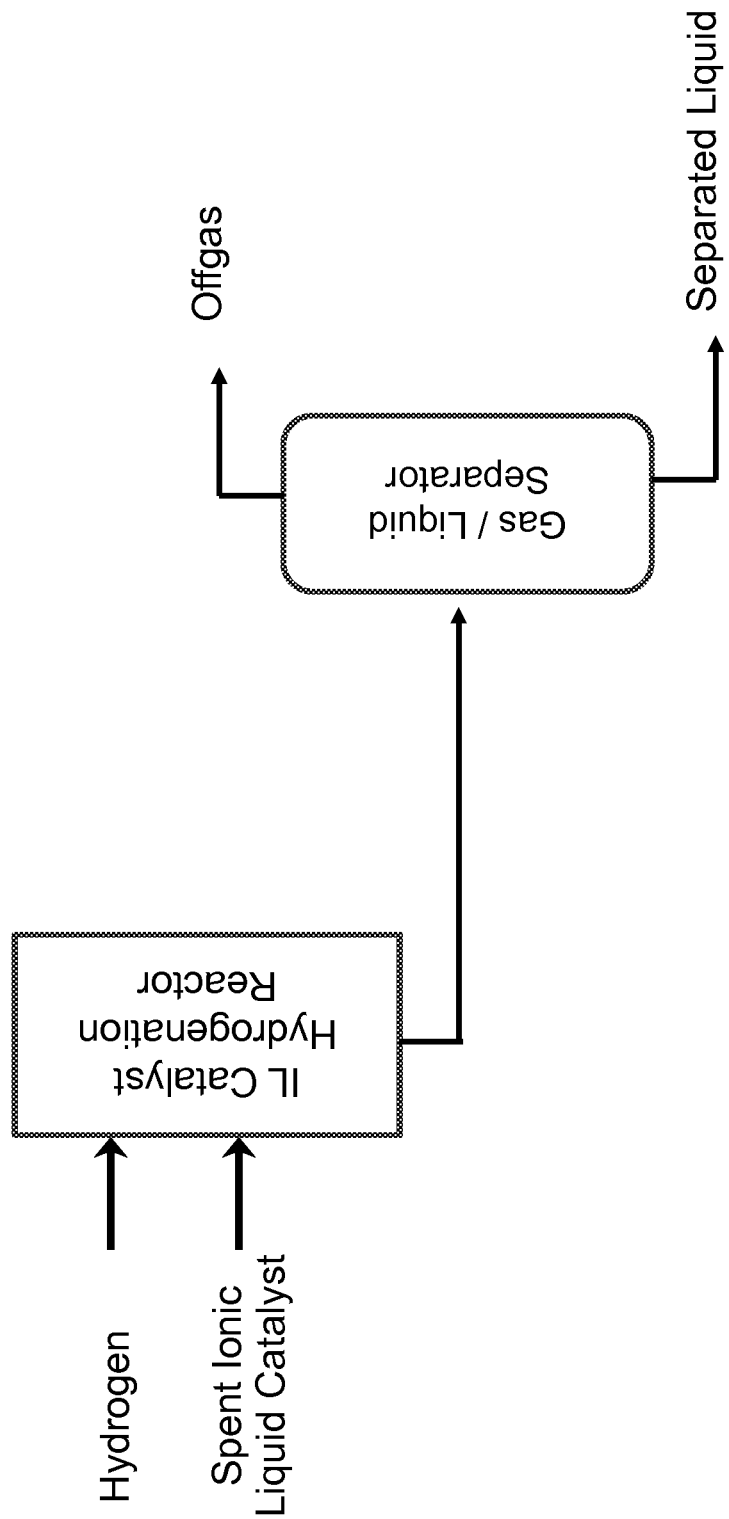
FIG. 6 is a diagram of a hydro-regeneration process without hydrocarbon extraction solvent.

Used ionic liquid catalyst containing 5 wt % conjunct polymer was regenerated by passing the ionic liquid catalyst through a hydrogenation reactor under $H_2$ atmosphere. 100% pure hydrogen gas was used. Hydro-regeneration of the ionic liquid catalyst was operated at 350° F. (177° C.), 350 psig, 5000 scf $H_2$/bbl ionic liquid catalyst, and 0.2 linear hourly space velocity (LHSV) in the presence of a hydrogenation catalyst containing Pt and Pd. The hydrogenation reactor effluent was separated into offgas and separated liquid streams in a gas/liquid separator as shown in FIG. 6. The separated liquid comprised regenerated ionic liquid catalyst and extracted conjunct polymer naphtha. At these conditions, 80 wt % of the conjunct polymer in the ionic liquid catalyst was converted to light material and the regenerated ionic liquid catalyst contained 1% conjunct polymer. The hydrogenation reactor offgas from the gas-liquid separation unit contained mostly $H_2$ and 6000 ppm of HCl. The offgas also contained 95% $H_2$ and 5 vol % of $C_3$-$C_6$ light hydrocarbons, while the bulk of light hydrocarbon was propane and isobutane. The purity of the hydrogen gas was dropped from 100% to 95% in one pass. In order to recycle the hydrogenation reactor offgas back to the hydrogenation unit, HCl and light hydrocarbon needed to be removed.

This example clearly shows that it will be highly desirable to have an efficient way to remove and reuse the HCl and hydrocarbon in the offgas. By removing the HCl and hydrocarbon in the offgas, the hydrogen gas can be recycled back to the hydrogenation reactor for repeated use. For removal of hydrogen chloride, a caustic treating method as shown in FIG. 2, would result in substantial loss of HCl and light hydrocarbon.

The separated liquid stream from the hydrogenation unit was further separated into the extracted conjunct polymer naphtha and regenerated ionic liquid catalyst. The regenerated ionic liquid catalyst was recycled back to the alkylation reactor for reuse.

Example 4

Improved HCl Recovery from Ionic Liquid Catalyst Hydrogenation with Hydrocarbon Extraction Solvent Used ionic liquid catalyst containing 4 wt % conjunct polymer from a alkylation reactor was regenerated by passing the ionic liquid catalyst through a hydrogenation reactor under $H_2$ atmosphere. 100% pure hydrogen gas was fed to the hydrogenation reactor. The hydrogenation reactor was operated at 350° F. (177° C.), 400 psig, 1500 scf $H_2$/bbl ionic liquid catalyst, and 2.0 LHSV in the presence of a hydrogenation catalyst containing Pt and Pd. The hydrogenation reactor effluent was separated into gas and liquid streams as shown in FIGS. 3 and 6. At these conditions, 25 wt % of the conjunct polymer in the ionic liquid catalyst was converted to light hydrocarbon material, and the regenerated ionic liquid catalyst contained 3 wt % conjunct polymer. The hydrogenation reactor offgas from the gas-liquid separator contained mostly $H_2$ and 1500 ppm of HCl. The offgas also contained 93 vol % $H_2$ and 7 vol % of $C_3$-$C_6$ light hydrocarbons, while about 85-90 vol % of the light hydrocarbon was propane and isobutane.

To demonstrate the concept of HCl extraction with hydrocarbon extraction solvent, n-hexane solvent was added to the hydrogenation reactor effluent at 2 and 4 times the volume of n-hexane to the ionic liquid catalyst flow. Then the mixture was further separated with the same separator. The analysis results of the offgas stream are summarized in Table 1 below.

TABLE 2

HCl Content in Hydrogenation Offgas
with Hydrocarbon Extraction Solvent

| | n-Hexane Flow Rate | | |
|---|---|---|---|
| | No n-Hexane Flow | 2.0 vol/vol n-Hexane/ Ionic liquid flow to the Hydrogenation Reactor Effluent | 4.0 vol/vol n-Hexane/ Ionic liquid flow to the Hydrogenation Reactor Effluent |
| HCl, ppm | 1500 | 500 | 300 |
| H2 Purity, vol % | 93 | 94 | 95 |
| C3-C6, vol % | 7 | 6 | 5 |

As we added n-hexane solvent to the hydrogenation reactor effluent, the hydrogen chloride content in the offgas dropped from 1500 ppm to 300 ppm. These results clearly suggested that the hydrogen chloride in the offgas stream can be extracted by adding hydrocarbon extraction solvent. The above set-up was a simple single stage separator. The extraction of the hydrogen chloride will improve further with multi-stage separation extractor, and possibly with counter-current flows of the two feeds to the separator.

Example 5

An Integrated Process for $H_2$ Recycle and HCl Recovery from Ionic Liquid Catalyst Hydrogenation This example shows an efficient $H_2$ purification/HCl recovery process using the feeds to the alkylation reactor. One embodiment is shown in FIG. 5.

The offgas (50) separated from the hydrogenated effluent (10) from the hydrogenation reactor (100) was mixed with isomerized olefins (12) and isoparaffin feed (65) comprising make-up isobutane in the amounts as shown in Table 3. The combined mixture was separated in a fractionation unit (200) that was a distillation column to separate the mixture into a) a gas fraction comprising a hydrogen gas (20), having low hydrogen chloride content, and b) a light hydrocarbon fraction comprising a hydrogen chloride (30). The light hydrocarbon fraction comprising a hydrogen chloride (30) contained the bulk (>90 wt %) of hydrogen chloride generated by the hydrogenation of used catalyst in the portion of the effluent (70) (in this example, ionic liquid catalyst). The compositions of the hydrogen gas streams before and after the HCl extraction (i.e., Hydrogenation Unit Offgas [offgas (50)] and Purified Gas Stream [gas fraction comprising a hydrogen gas (20)], respectively) are shown in Table 3.

The gas fraction comprising a hydrogen gas (20) (also referred to as the purified hydrogen gas stream) was recycled back to the hydrogenation reactor (100) for regeneration of used catalyst in the portion of the effluent (70), in this case a used ionic liquid catalyst. The used ionic liquid catalyst containing 5 wt % conjunct polymer was passed through the hydrogenation reactor (100) at 350° F. (177° C.), 450 psig, 5000 scf $H_2$/bbl ionic liquid catalyst using recycled hydrogen gas, and 0.2 weight hourly space velocity (WHSV) in the presence of a hydrogenation catalyst containing Pt and Pd. At these conditions, 80 wt % of the conjunct polymer in the used ionic liquid catalyst was converted to light material and the regenerated ionic liquid catalyst contained 1% conjunct polymer. The hydrogenation reactor offgas [offgas (50)] from the gas-liquid separation unit [Separator (400)] contained 6000 ppm of HCl and substantial amounts of hydrogen and light hydrocarbon.

TABLE 3

Composition of Recycle $H_2$ Stream and Alkylation Reactor Feed with Recovered HCl

| | Hydrogenation Unit Offgas (Offgas (50)) | Isomerized Olefins (12) | Make-Up Isobutane (Isoparaffin feed (65)) | Purified Gas Stream (Gas fraction comprising a hydrogen gas (20)) | HCl-Rich Hydrocarbon Feed (Light hydrocarbon fraction comprising a hydrogen chloride (30)) |
|---|---|---|---|---|---|
| | | | Material Balance | | |
| HCl, mole/day | 0.605 | 0 | 0 | 0.024 | 0.581 |
| $H_2$, mole/day | 76 | 6 | 0 | 82 | 0.02 |
| $C_3^=$, mole/day | 0 | 170 | 0 | 0.35 | 169 |
| $C_3$, mole/day | 12 | 74 | 44 | 16 | 113 |
| $C_4^=$, mole/day | 0 | 215 | 0 | 0 | 215 |
| $iC_4$, mole/day | 13 | 165 | 243 | 22 | 398 |
| $nC_4$, mole/day | 1 | 97 | 28 | 1 | 124 |
| | | | HCl Concentration | | |
| HCl Recovery, wt % | Source | — | — | 4% | 96% |
| HCl, ppm | 6000 | — | — | 200 | — |

The results in Table 3 show that 96% of the hydrogen chloride from the hydro-regeneration offgas [offgas (50)] was recovered by our integrated process using a hydrocarbon extraction solvent (25). The hydro-regeneration offgas [offgas (50)] had very high concentration of hydrogen chloride, 6000 ppm. After the fractionation, the Purified Gas Stream [Gas fraction comprising a hydrogen gas (20)] contains only 200 ppm of HCl and the Purified Gas Stream was recycled to the hydrogenation reactor (100). This process also produced a desirable light hydrocarbon fraction comprising a hydrogen chloride (30), with little residual hydrogen, and the light hydrocarbon fraction comprising a hydrogen chloride (30) was sent to the alkylation reactor (300).

This example showed that maximum recovery of hydrogen chloride could be achieved with extensive use of hydrocarbon extraction solvent where both make-up isobutane and olefin alkylation feeds are used to extract hydrogen chloride from the hydrogenation offgas. The efficient recovery and recycle of hydrogen chloride greatly lowers the operating cost and reduces the quantity of make-up HCl that needs to be added to the process.

The transitional term "comprising", which is synonymous with "including," "containing," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

For the purposes of this specification and appended claims, unless otherwise indicated, all numbers expressing quantities, percentages or proportions, and other numerical values used in the specification and claims, are to be understood as being modified in all instances by the term "about." Furthermore, all ranges disclosed herein are inclusive of the endpoints and are independently combinable. Whenever a numerical range with a lower limit and an upper limit are disclosed, any number falling within the range is also specifically disclosed.

Any term, abbreviation or shorthand not defined is understood to have the ordinary meaning used by a person skilled in the art at the time the application is filed. The singular forms "a," "an," and "the," include plural references unless expressly and unequivocally limited to one instance.

All of the publications, patents and patent applications cited in this application are herein incorporated by reference in their entirety to the same extent as if the disclosure of each individual publication, patent application or patent was specifically and individually indicated to be incorporated by reference in its entirety.

This written description uses examples to disclose the invention, including the best mode, and also to enable any person skilled in the art to make and use the invention. Many modifications of the exemplary embodiments of the invention disclosed above will readily occur to those skilled in the art. Accordingly, the invention is to be construed as including all structure and methods that fall within the scope of the appended claims. Unless otherwise specified, the recitation of a genus of elements, materials or other components, from which an individual component or mixture of components can be selected, is intended to include all possible sub-generic combinations of the listed components and mixtures thereof.

It is claimed:

1. An alkylation process unit, comprising:
   a. a fractionation unit (200) for separating a hydrogen gas and a hydrogen chloride from an offgas (50) of a hydrogenation reactor (100) that regenerates a used ionic liquid catalyst; and
   b. a first connection between the fractionation unit (200) and the hydrogenation reactor (100) for transmitting at least a portion comprising the hydrogen gas to the hydrogenation reactor (100);
   c. a second connection between the fractionation unit (200) and an alkylation reactor (300) to transmit at least a second portion comprising the hydrogen chloride to the alkylation reactor (300); and
   d. an inlet wherein a hydrocarbon extraction solvent (25) is fed to the fractionation unit (200) or to a separator (400) that is located between the hydrogenation reactor (100) and the fractionation unit (200).

2. The alkylation process unit of claim 1, wherein the fractionation unit (200) is a distillation column.

3. The alkylation process unit of claim 1, wherein the inlet is at a location above where the hydrogen gas and the hydrogen chloride are fed to the fractionation unit (200).

4. The alkylation process unit of claim 1, wherein the hydrocarbon extraction solvent (25) is fed to the separator (400).

5. The alkylation process unit of claim 1, wherein the hydrogenation reactor (100) comprises a hydrogenation catalyst containing Pt and Pd.

6. The alkylation process unit of claim 1, wherein the used ionic liquid catalyst is a chloroaluminate ionic liquid catalyst.

7. The alkylation process unit of claim 1, additionally comprising an ionic liquid catalyst and hydrocarbon separator (500) which separates the offgas (50) into a light hydrocarbon fraction comprising the hydrogen chloride (30), an extracted conjunct polymer naphtha (45), and an ionic liquid catalyst stream (60).

8. The alkylation process unit of claim 1, additionally comprising a third connection between a product treatment unit and the second connection, wherein the second portion is mixed with a recycled stream, from the product treatment unit, comprising a mixture of a gaseous hydrogen chloride and a propane.

9. The alkylation process unit of claim 1, wherein the hydrocarbon extraction solvent (25) is fed to the fractionation unit (200).

10. An alkylation process unit, comprising:
    a. a fractionation unit (200) for separating a hydrogen gas and a hydrogen chloride from an offgas (50) of a hydrogenation reactor (100) that regenerates a used ionic liquid catalyst; and
    b. a first connection between the fractionation unit (200) and the hydrogenation reactor (100) for transmitting at least a portion comprising the hydrogen gas to the hydrogenation reactor (100);
    c. a second connection between the fractionation unit (200) and an alkylation reactor (300) to transmit at least a second portion comprising the hydrogen chloride to the alkylation reactor (300); and
    d. a third connection between a product treatment unit and the second connection, wherein the second portion is mixed with a recycled stream, from the product treatment unit, comprising a mixture of a gaseous hydrogen chloride and a propane.

11. The alkylation process unit of claim 10, wherein the fractionation unit (200) is a distillation column.

12. The alkylation process unit of claim 10, additionally comprising an inlet wherein a hydrocarbon extraction solvent (25) is fed to the fractionation unit (200) or to a separator (400) that is located between the hydrogenation reactor (100) and the fractionation unit (200).

13. The alkylation process unit of claim 12, wherein the inlet is at a location above where the hydrogen gas and the hydrogen chloride are fed to the fractionation unit (200).

14. The alkylation process unit of claim 10, additionally comprising a separator (400) between the hydrogenation reactor (100) and the fractionation unit (200).

15. The alkylation process unit of claim 10, wherein the hydrogenation reactor (100) comprises a hydrogenation catalyst containing Pt and Pd.

16. The alkylation process unit of claim 10, wherein the used ionic liquid catalyst is a chloroaluminate ionic liquid catalyst.

17. The alkylation process unit of claim 10, additionally comprising an ionic liquid catalyst and hydrocarbon separator (500) which separates the offgas (50) into a light hydrocarbon fraction comprising the hydrogen chloride (30), an extracted conjunct polymer naphtha (45), and an ionic liquid catalyst stream (60).

* * * * *